(12) United States Patent
Antelman

(10) Patent No.: US 8,647,647 B2
(45) Date of Patent: Feb. 11, 2014

(54) SILVER OXIDE FORMULATIONS HAVING IMPROVED WHITENESS CHARACTERISTICS

(75) Inventor: Perry Antelman, Sharon, MA (US)

(73) Assignee: Aidance Skincare and Topical Solutions, LLC, Woonsocket, RI (US)

( * ) Notice: Subject to any disclaimer, the term of this patent is extended or adjusted under 35 U.S.C. 154(b) by 293 days.

(21) Appl. No.: 12/841,031

(22) Filed: Jul. 21, 2010

(65) Prior Publication Data

US 2011/0020468 A1 Jan. 27, 2011

Related U.S. Application Data

(60) Provisional application No. 61/227,297, filed on Jul. 21, 2009.

(30) Foreign Application Priority Data

Mar. 9, 2010 (GB) .................................. 1003870.1

(51) Int. Cl.

| | |
|---|---|
| A61K 8/02 | (2006.01) |
| A61K 31/315 | (2006.01) |
| A61K 31/28 | (2006.01) |
| A61K 9/50 | (2006.01) |
| A61K 33/32 | (2006.01) |
| A01N 59/16 | (2006.01) |
| A01N 55/02 | (2006.01) |
| C01G 7/00 | (2006.01) |
| C22B 17/00 | (2006.01) |
| C22B 43/00 | (2006.01) |
| A61F 13/02 | (2006.01) |
| A61L 15/16 | (2006.01) |
| B01F 1/00 | (2006.01) |

(52) U.S. Cl.
USPC ........... 424/401; 424/445; 424/446; 424/447; 424/448; 424/449; 424/484; 424/486; 424/502; 424/600; 424/617; 424/618; 424/642; 423/23; 423/27; 423/99; 423/101; 423/622; 514/494; 514/495

(58) Field of Classification Search
USPC ......... 424/445, 446, 447, 448, 449, 484, 486, 424/502; 423/23, 27, 99, 101, 109, 604, 423/622
See application file for complete search history.

(56) References Cited

U.S. PATENT DOCUMENTS

| | | | |
|---|---|---|---|
| 2,521,713 A | | 9/1950 | Goetz |
| 4,489,223 A | * | 12/1984 | Puckett et al. ........... 191/12.2 R |
| 4,849,223 A | * | 7/1989 | Pratt et al. .................... 424/409 |
| 5,571,520 A | | 11/1996 | Antelman |

(Continued)

FOREIGN PATENT DOCUMENTS

| | | | | |
|---|---|---|---|---|
| EP | 0427858 A1 | * | 5/1991 | ............. A01N 25/08 |
| EP | 04278558 A1 | * | 5/1991 | ............. A01N 25/08 |

OTHER PUBLICATIONS

Zinc oxide. Datasheet [online]. Hakusuitech Ltd., 1998-2006 [retrieved on Apr. 8, 2012]. Retrieved from the Internet: <URL: http://www.hakusui.co.jp/e/Products/Esanka.html>.*

(Continued)

*Primary Examiner* — Jane C Oswecki (57) ABSTRACT

A topical formulation for application to exposed body tissue, the formulation comprising a silver(II) oxide and zinc oxide, intimately dispersed within a carrier medium.

20 Claims, 3 Drawing Sheets

(56) References Cited

U.S. PATENT DOCUMENTS

| | | | |
|---|---|---|---|
| 6,258,385 B1 | 7/2001 | Antelman | |
| 6,485,755 B1 | 11/2002 | Antelman | |
| 6,645,531 B1 | 11/2003 | Antelman | |
| 6,669,966 B1 | 12/2003 | Antelman | |
| 2004/0247696 A1 | 12/2004 | Antelman | |
| 2006/0105057 A1 | 5/2006 | Antelman | |
| 2006/0171971 A1* | 8/2006 | Marsh et al. | 424/401 |
| 2006/0246149 A1* | 11/2006 | Buchholz et al. | 424/603 |
| 2008/0050452 A1 | 2/2008 | Chen | |
| 2009/0110750 A1 | 4/2009 | Greener | |
| 2009/0191139 A1* | 7/2009 | Shimizu et al. | 424/63 |

OTHER PUBLICATIONS

Zinc oxide. Datasheet [online]. Hakusuitech Ltd., 1998-2006, [retrieved on Apr. 8, 2012]. Retrieved from the Internet: <URL: http://www.hakusui.co.jp/e/Products/Esanka.html>.*

International Search Report for PCT/IB10/02024 (mailed Dec. 22, 2010).

International Search Written Opinion for PCT/IB10/02024 (mailed Dec. 22, 2010).

International Preliminary Report on Patentability for PCT/IB10/02024 (mailed Feb. 22, 2012).

* cited by examiner

Figure 5

SILVER OXIDE FORMULATIONS HAVING IMPROVED WHITENESS CHARACTERISTICS

CROSS-REFERENCE TO RELATED APPLICATIONS

This application draws priority from U.K. Patent Application No. GB1003870.1, filed Mar. 9, 2010; this application draws priority from U.S. Provisional Patent Application Ser. No. 61/227,297, filed Jul. 21, 2009, which is incorporated by reference for all purposes as if fully set forth herein.

FIELD AND BACKGROUND OF THE INVENTION

The present invention relates to anti-microbial silver oxide formulations, and, more particularly, to anti-microbial silver oxide formulations having improved whiteness characteristics.

Silver and various silver derivatives are known to have anti-microbial properties. Commercial applications of such products include impregnated bandages, mold-free and odor-free textiles, and various kinds of skin creams. In addition, there exist several oral medicines that utilize silver as an active ingredient, including anti-smoking lozenges containing silver acetate ($AgC_2H_3O_2$), breath mints coated with silver, and silver nitrate solutions for treating gum disease.

One particularly effective group of silver derivatives is the group of silver oxides. Of the oxides, silver(II) oxide is known to be more effective than $Ag_2O$ silver(I) oxide.

Skin creams containing silver(II) oxide have been reported to be efficacious in treating various medical conditions, including genital herpes, oral herpes, vaginitis, vaginal yeast infections, foot and nail fungus, burns, warts, and skin infections. These skin formulations are characterized by their creaminess and ease of application, which, inter alia, enables the polyvalent silver oxide to intimately contact the skin surface.

Disadvantageously, however, the various forms of silver oxide, and silver(II) oxide in particular, are dark gray or charcoal gray powders, and are thus extremely hard to hide within white creams used in various cosmetic or pharmaceutical topical applications. Moreover, the dark silver oxide particles may stain skin and clothing.

The inventor has perceived a need for further improvements in silver oxide formulations, and the subject matter of the present disclosure and claims is aimed at fulfilling this need.

SUMMARY OF THE INVENTION

According to the teachings of the present invention there is provided a topical formulation for application to exposed body tissue, the formulation including a silver oxide and zinc oxide, intimately dispersed within a carrier medium.

According to another aspect of the present invention there is provided a topical formulation for application to exposed body tissue, the formulation including a silver oxide and zinc oxide, the silver oxide and the zinc oxide intimately dispersed within a carrier medium, wherein the silver oxide includes, largely includes, predominantly includes, or consists essentially of a silver(II) oxide.

According to further features in the described preferred embodiments, the formulation contains at least 0.05%, by weight, of the silver oxide, and at least 0.05%, by weight, of the zinc oxide.

According to still further features in the described preferred embodiments, the formulation contains less than 25%, less than 20%, less than 15%, less than 12%, less than 10%, or less than 8%, by weight, of the zinc oxide.

According to still further features in the described preferred embodiments, a ratio of the zinc oxide to the silver oxide is at least 0.5:1, 1:1, 2:1, 3:1, or 6:1, by weight.

According to still further features in the described preferred embodiments, a ratio of the zinc oxide to the silver oxide is less than 100:1, 50:1, 20:1, 12:1, 10:1, or 8:1, by weight.

According to still further features in the described preferred embodiments, the formulation contains less than 3%, by weight, of the silver oxide.

According to still further features in the described preferred embodiments, the formulation contains at least 0.05%, at least 0.10%, at least 0.2%, or at least 0.25%, by weight, of the silver oxide.

According to still further features in the described preferred embodiments, the carrier medium includes an oleaginous material.

According to still further features in the described preferred embodiments, the oleaginous material includes a wax.

According to still further features in the described preferred embodiments, the oleaginous material includes beeswax.

According to still further features in the described preferred embodiments, the topical formulation further includes a liquid wax ester such as jojoba oil or hydrogenated jojoba oil.

According to still further features in the described preferred embodiments, the silver oxide and zinc oxide are selected, and the silver oxide and the zinc oxide are dispersed within the carrier medium, whereby a whiteness of the formulation satisfies an equation: $L^* \geq (L_0^*) + 2$, wherein $L_0^*$ is a baseline whiteness value of the formulation, without the zinc oxide, and $L^*$ is a whiteness value of the formulation, including the zinc oxide.

According to still further features in the described preferred embodiments, the silver oxide, the zinc oxide, and the carrier medium are selected, and the silver oxide and the zinc oxide are dispersed within the carrier medium, whereby the whiteness value $L^*$ is at least 75, at least 78, at least 80, at least 82, or at least 84.

According to still further features in the described preferred embodiments, the content of the silver oxide is at least 0.5%, and the silver oxide, the zinc oxide, and the carrier medium are selected, and the silver oxide and the zinc oxide are dispersed within the carrier medium, whereby the whiteness value $L^*$ of the formulation is at least 80, at least 82, or at least 84.

According to still further features in the described preferred embodiments, the content of the silver oxide is at least 1.0%, and the silver oxide, the zinc oxide, and the carrier medium are selected, and the silver oxide and the zinc oxide are dispersed within the carrier medium, whereby the whiteness value $L^*$ of the formulation is at least 72, at least 75, at least 78, at least 80, at least 82, or at least 84.

According to still further features in the described preferred embodiments, the silver oxide, the zinc oxide, and the carrier medium are selected, and the silver oxide and the zinc oxide are dispersed within the carrier medium, whereby the whiteness value $L^*$ of the formulation is at least 82 or at least 84.

According to still further features in the described preferred embodiments, the carrier medium includes an aqueous phase.

According to still further features in the described preferred embodiments, the carrier medium is selected whereby the formulation is a water-based cream or lotion.

According to still further features in the described preferred embodiments, the formulation contains zinc oxide within a range of about 0.02% to about 25%, by weight, and the silver oxide largely includes a silver (II) oxide, the formulation including at least about 0.02% of the silver (II) oxide, by weight.

According to still further features in the described preferred embodiments, the formulation contains at least about 0.05% of the silver (II) oxide, and less than about 12%, less than about 10%, less than about 8%, or less than about 6% of the zinc oxide, by weight.

According to still further features in the described preferred embodiments, the formulation contains at least 0.05%, by weight, of silver(II) oxide, and the ratio of the zinc oxide to the silver(II) oxide is less than 12:1, less than 10:1, less than 8:1, or less than 6:1, by weight.

According to still further features in the described preferred embodiments, the formulation containing at least 0.1%, at least 0.25%, at least 0.5%, at least 0.75%, or at least 1%, by weight, of the silver(II) oxide.

According to still further features in the described preferred embodiments, the formulation further includes any of the materials described herein, either individually or in combination with any other material, in any structure or form.

According to yet another aspect of the present invention there is provided a wound dressing including any of the topical formulations described herein.

According to still further features in the described preferred embodiments, the wound dressing includes an adhesive-containing bandage, a cotton roll bandage, or a gelable polymer.

According to yet another aspect of the present invention there is provided a method of producing a topical formulation for application to exposed body tissue, the formulation including a silver oxide and zinc oxide, intimately dispersed within a carrier medium substantially as described herein, the method including any feature described, either individually or in combination with any feature, in any configuration.

According to yet another aspect of the present invention there is provided a method of effecting a treatment of skin tissue, substantially as described herein, the method including any feature described, either individually or in combination with any feature, in any configuration.

According to further features in the described preferred embodiments, the method includes the steps of: (a) providing a formulation including: (i) a silver oxide such as a silver(II) oxide; (ii) zinc oxide, and (iii) a carrier medium, wherein the formulation contains at least 0.05%, by weight, of the silver oxide, and less than 25%, less than 20%, less than 15%, less than 12%, less than 10%, or less than 8% of the zinc oxide by weight, of the zinc oxide, and wherein the silver oxide and the zinc oxide are intimately dispersed within the carrier medium, and (b) applying the formulation to the skin tissue to effect the treatment of the skin tissue.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 5 provides top view photographs of Petri dishes containing oil-based formulations and identically grown cultures according to a modified pour plate method, wherein:

DESCRIPTION OF THE PREFERRED EMBODIMENTS

Before explaining at least one embodiment of the invention in detail, it is to be understood that the invention is not limited in its application to the details of construction and the arrangement of the components set forth in the following description. The invention may be capable of other embodiments or of being practiced or carried out in various ways. Also, it is to be understood that the phraseology and terminology employed herein is for the purpose of description and should not be regarded as limiting.

The medical device of the present invention contains both a silver oxide compound and zinc oxide, preferably in a carrier medium that may be a water-based cream or lotion, or an ointment that may include a wax and/or an oil. The formulation may include an emulsion, or be substantially emulsion-based.

The inventive silver oxide based medical device may have a generally white appearance. At lower ratios of whitening agent to silver oxide, the appearance of the medical device may be off-white or grayish.

I have found that silver(II) oxide, despite being an extremely reactive material, does not deleteriously interact with zinc oxide within the formulation. I have also found that the zinc oxide does not appear to reduce or appreciably reduce the anti-microbial efficacy of the silver(II) oxide. This appears to be particularly surprising, because zinc oxide is used in various coating applications, and might be expected to cover or block the silver(II) oxide particles, thereby reducing the contact between the silver(II) oxide particles and the microorganisms.

Moreover, I have surprisingly discovered that within a specified range of weight ratios and/or compositions, the silver oxide based formulation is highly spreadable, despite the presence of the chalky zinc oxide. I have found that silver oxide-zinc oxide formulations containing more than 25% zinc oxide, by weight, may display poor spreadability, and may also be less efficacious from an anti-microbial standpoint. In some formulations, a zinc oxide content of more than 20%, by weight, may exhibit such deleterious properties.

I have found that for formulations within a particular range of zinc oxide to silver oxide weight ratios, or having a particular range of zinc oxide and silver oxide contents, the zinc oxide acts to appreciably whiten the inventive formulations. However, above this particular range of zinc oxide to silver oxide weight ratios, or above a particular amount of zinc oxide, the whitening effect of the zinc oxide may become substantially insignificant.

Whiter formulations tend to be more aesthetically pleasing, and it would appear that such whiter formulations would tend to promote less staining of fabric such as clothes. However, I have surprisingly found that when formulations containing zinc oxide mixed with a silver oxide (such as a silver (II) oxide) are disposed on a fabric, conventional laundering of the fabric yields stains having a lightness that may not monotonically correlate with the lightness of the initial stain, prior to the laundering.

Figure 1:
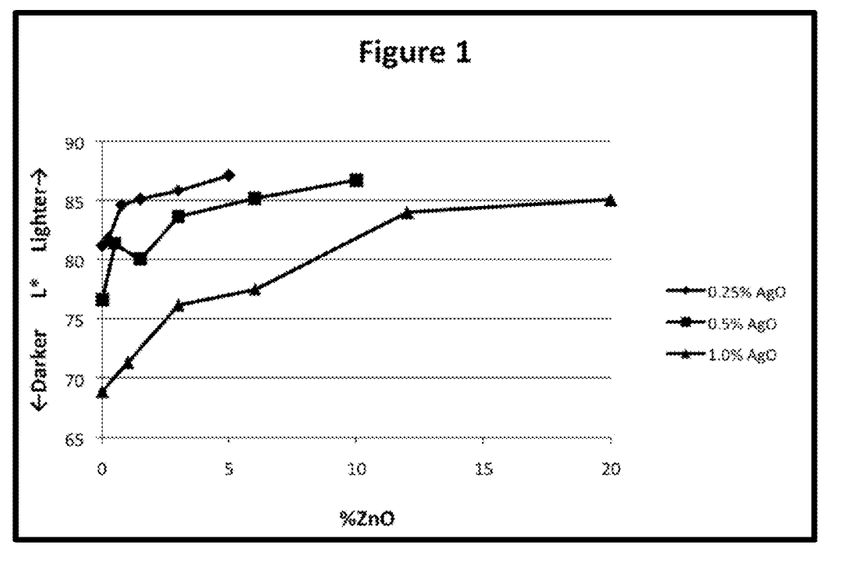
FIG. 1 is a graph plotting whiteness of cloth swatches stained with formulations containing varying concentrations zinc oxide and silver(II) oxide, as a function of the weight content of zinc oxide within the formulations.

With reference now to FIG. 1, FIG. 1 is a graph plotting formulation whiteness or luminance (expressed as L*) as a function of zinc oxide concentration (in weight percent) within the formulation. The whiteness parameter L* has been specified by the International Commission on Illumination (Commission Internationale d'Eclairage, or CIE) to achieve perceptual uniformity, and the L* component thereof has been determined to closely match human perception of lightness. Regarding the scale of L*, the luminance is expressed as a percentage, wherein L*=0 represents black, and L*=100 represents diffuse white.

In FIG. 1, formulations containing three concentrations of silver(II) oxide were tested: 0.25%, 0.5%, and 1%, by weight, respectively. As may be seen from the data in Table 1 and from FIG. 1, the formulation whiteness (L*) increases substantially monotonically with increasing concentration of zinc oxide. However, appreciable differential increases in the formulation whiteness (L*) are typically obtained when the zinc oxide concentration is less than about 12%, less than about 10%, less than about 8%, or less than about 6% zinc oxide, by weight.

TABLE 1

| 0.25% silver(II) oxide | | 0.5% silver(II) oxide | | 1% silver(II) oxide | |
| --- | --- | --- | --- | --- | --- |
| % zinc oxide | L* | % zinc oxide | L* | % zinc oxide | L* |
| 0 | 81.16 | 0 | 76.62 | 0 | 68.89 |
| 0.25 | 81.81 | 0.5 | 81.39 | 1 | 71.34 |
| 0.75 | 84.58 | 1.5 | 80.04 | 3 | 76.20 |
| 1.5 | 85.11 | 3 | 83.65 | 6 | 77.51 |
| 3 | 85.84 | 6 | 85.17 | 12 | 83.98 |
| 5 | 87.12 | 10 | 86.73 | 20 | 85.09 |

Figure 2:
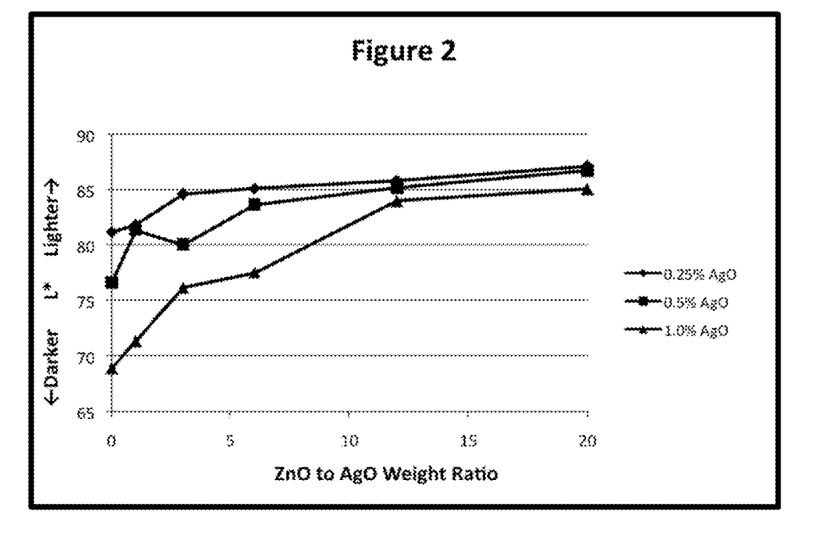
FIG. 2 is a graph plotting whiteness of the cloth swatches as a function of the weight ratio of zinc oxide to silver(II) oxide within each of the above formulations.

FIG. 2 is a graph plotting formulation whiteness (expressed as L*) as a function of the weight ratio of zinc oxide to silver(II) oxide within each formulation.

As may be seen from the data in Table 2 and from FIG. 2, the formulation whiteness (L*) increases substantially monotonically with increasing ratio of zinc oxide to silver(II) oxide. However, appreciable differential increases in the formulation whiteness (L*) are typically obtained when the ratio of zinc oxide to silver(II) oxide within the formulation is less than about 15:1, less than about 12:1, less than about 10:1, less than about 8:1, or less than about 6:1. Below a ratio of about 20:1, the differential increase in the formulation whiteness is less substantial.

TABLE 2

| 0.25% silver(II) oxide | | 0.5% silver(II) oxide | | 1% silver(II) oxide | |
| --- | --- | --- | --- | --- | --- |
| ratio of ZnO to silver(II) oxide | L* | ratio of ZnO to silver(II) oxide | L* | ratio of ZnO to silver(II) oxide | L* |
| 0 | 81.16 | 0 | 76.62 | 0 | 68.89 |
| 0.25 | 81.81 | 0.5 | 81.39 | 1 | 71.34 |
| 0.75 | 84.58 | 1.5 | 80.04 | 3 | 76.20 |
| 1.5 | 85.11 | 3 | 83.65 | 6 | 77.51 |
| 3 | 85.84 | 6 | 85.17 | 12 | 83.98 |
| 5 | 87.12 | 10 | 86.73 | 20 | 85.09 |

I have surprisingly found that when formulations containing zinc oxide mixed with a silver oxide (such as a silver(II) oxide) are disposed on a fabric, conventional laundering of the fabric yields stains that may not monotonically correlate with the lightness of the initial stain, prior to the laundering. Table 3 provides whiteness (L*) as a function of concentration of zinc oxide, for a white fabric impregnated with the formulations provided in Table 1, after the fabric has undergone a staining and laundering procedure.

The following procedure was used:
Cut a 7×7 cm piece of fabric from a white cotton T-shirt to produce a cloth swatch;
1. Weigh the cloth swatch;
2. Place cloth swatch on a clean paper towel to absorb any extraneous oil from the staining procedure;
3. Apply 400 mg of staining sample to the back of spatula;
4. Spread sample evenly over 90% of cloth surface using spatula, taking care
   a. not to stain edges, and
   b. to use the entire staining sample;
5. Re-weigh cloth swatch to insure complete transfer of the sample (typically weighs an additional ~400 mg);
6. Allow the cloth to absorb the sample for 24 hours in an open air environment at room temperature (65-75° F.);
7. Place cloth in 650-700 ml of warm detergent/water solution (regular tap water and Lestoil® brand detergent/stain remover or similar);
   a. Solution is prepared using 10 ml of detergent for every liter of water;
   b. Solution is drawn anew from a stock solution for each sample;
   c. Stock solution is warmed to ~130° F.;
8. Mix cloth-containing solution for 10 minutes using mixer operating at 300 rpm;
9. Rinse cloth by placing in beaker of clean water. Remove cloth, and repeat rinsing procedure for a total of three rinses, each time using new clean water;
10. Pin swatches to uniform flat wall;
    a. Pin only the unstained edges;
    b. Place in open air environment;
    c. Maintain swatches at room temperature (65-75° F.); and 11. Store swatches in a lightproof pouch until ready to measure with colorimetric instrument.

The whiteness of the various samples was measured using a Color Cue® 2.1 colorimetric instrument (Pantone, Inc.). A clear plastic wrap was placed over each sample. The colorimeter was then lightly pressed onto the wrap and the color was recorded. The L* reading was used to indicate the relative lightness of the stain with respect to other samples. Readings were recorded from 3 separate areas on the cloth sample, and the obtained values were averaged.

The formulations used in the staining and laundering procedure contained three concentrations of silver(II) oxide: 0.25%, 0.5%, and 1%, by weight, as described with respect to Table 1 hereinabove. With reference now to the values provided in Table 3, and plotted in FIG. 3, it is observed that at low zinc oxide content, the whiteness (L*) of the laundered cloth swatches increases with increasing concentration of zinc oxide. However, at each of the three concentrations of silver oxide, a maximum whiteness is observed at zinc oxide contents of about 0.75%, 1.5%, and 6%, respectively. Above these values, the whiteness (L*) of the laundered cloth swatches levels off, or may even decrease somewhat with increasing concentration of zinc oxide.

The presently preferred zinc oxide content in the formulations of the present invention may be heavily dependent on the silver oxide content within the formulation, which may be at least 0.05%, at least 0.1%, at least 0.25%, at least 0.5%, at least 0.75%, at least 1%, or at least 3%, by weight. However, the preferred zinc oxide content may depend upon the particular composition of the formulation, upon the composition of the base material(s), and upon other formulation characteristics. Generally, however, the presently preferred zinc oxide content in the formulations of the present invention may be at least 0.5%, at least 0.75%, at least 1%, or at least 3%, by weight. The presently preferred zinc oxide content in the formulations of the present invention may be less than 20%, by weight, and more typically, less than about 12%, less than about 10%, less than about 8% zinc oxide, or less than about 6% zinc oxide.

TABLE 3

| 0.25% silver(II) oxide | | 0.5% silver(II) oxide | | 1% silver(II) oxide | |
| --- | --- | --- | --- | --- | --- |
| % zinc oxide | L* | % zinc oxide | L* | % zinc oxide | L* |
| 0 | 84.38 | 0 | 80.52 | 0 | 71.39 |
| 0.25 | 86.96 | 0.5 | 83.31 | 1 | 73.81 |
| 0.75 | 87.66 | 1.5 | 83.96 | 3 | 74.85 |
| 1.5 | 87.18 | 3 | 83.19 | 6 | 77.38 |
| 3 | 86.67 | 6 | 83.73 | 12 | 77.17 |
| 5 | 86.95 | 10 | 83.22 | 20 | 75.64 |

Figure 4:
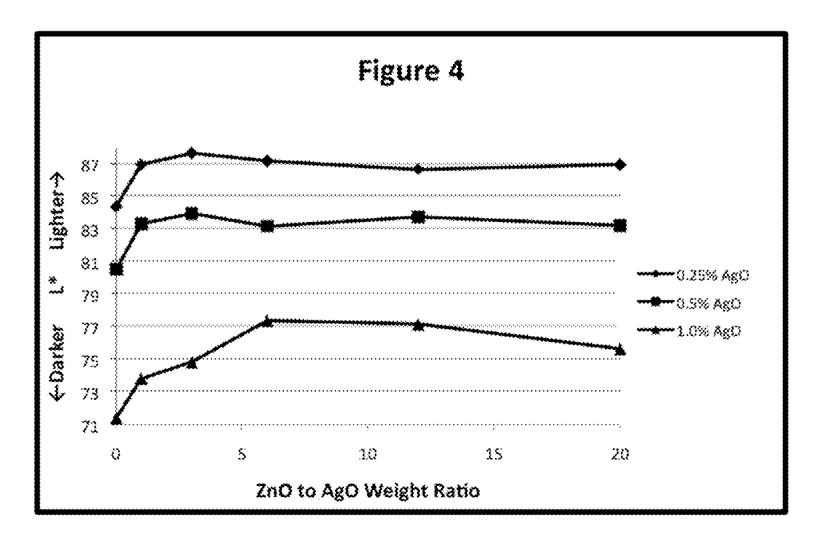
FIG. 4 is a graph plotting whiteness of the laundered cloth swatches as a function of the weight ratio of zinc oxide to silver(II) oxide within the staining formulations initially applied to the swatches.
Figures 5A, 5C:
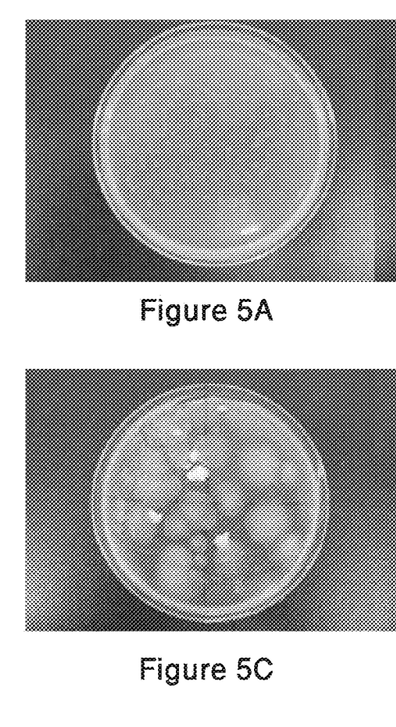
FIG. 5A shows a cultured Petri dish after being exposed to a formulation containing 1.0% AgO and 7.0% ZnO.
FIG. 5C shows a cultured Petri dish after being exposed to a formulation containing 7.0% ZnO and no Ago.
Figure 5B:
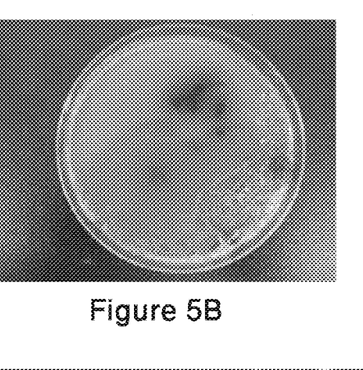
FIG. 5B shows a cultured Petri dish after being exposed to a formulation containing 1.0% AgO and no ZnO.
Figure 5D:
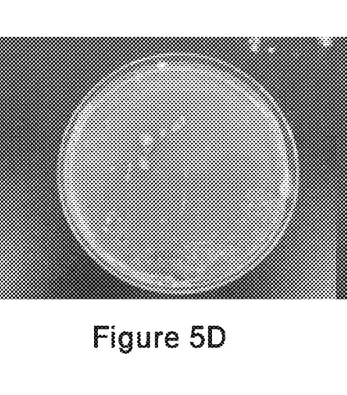
FIG. 5D shows a cultured Petri dish after being exposed to a formulation containing 1.0% AgO and 14.0% ZnO.
Figure 5E:
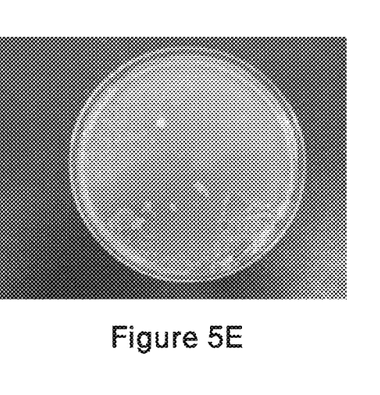
FIG. 5E shows a cultured Petri dish after being exposed to a formulation containing 0.84% AgO and 28.0% ZnO.

FIG. 4 is a graph plotting formula whiteness (expressed as L*) as a function of the weight ratio of zinc oxide to silver(II) oxide within each formulation used in the staining and laundering procedure described hereinabove. As may be seen from FIG. 4 and the corresponding data in Table 4, the formulation whiteness (L*) generally increases appreciably with increasing ratio of zinc oxide to silver(II) oxide, at low weight ratios of zinc oxide to silver(II) oxide. Surprisingly, however, above a weight ratio of zinc oxide to silver(II) oxide of 1:1, 3:1, 5:1, or 6:1, the formulation whiteness generally increases only marginally, or fails to increase, with increasing ratio of zinc oxide to silver(II) oxide. Indeed, above a weight ratio of zinc oxide to silver(II) oxide of 8:1, 10:1, or perhaps most clearly, 12:1, the formulation whiteness may be substantially constant, or may even decrease with increasing ratio of zinc oxide to silver(II) oxide.

TABLE 4

| 0.25% silver(II) oxide | | 0.5% silver(II) oxide | | 1% silver(II) oxide | |
| --- | --- | --- | --- | --- | --- |
| ratio of ZnO to silver(II) oxide | L* | ratio of ZnO to silver(II) oxide | L* | ratio of ZnO to silver(II) oxide | L* |
| 0 | 84.38 | 0 | 80.52 | 0 | 71.39 |
| 1 | 86.96 | 1 | 83.31 | 1 | 73.81 |
| 3 | 87.66 | 3 | 83.96 | 3 | 74.85 |
| 6 | 87.18 | 6 | 83.19 | 6 | 77.38 |
| 12 | 86.67 | 12 | 83.73 | 12 | 77.17 |
| 20 | 86.95 | 20 | 83.22 | 20 | 75.64 |

Figure 3:
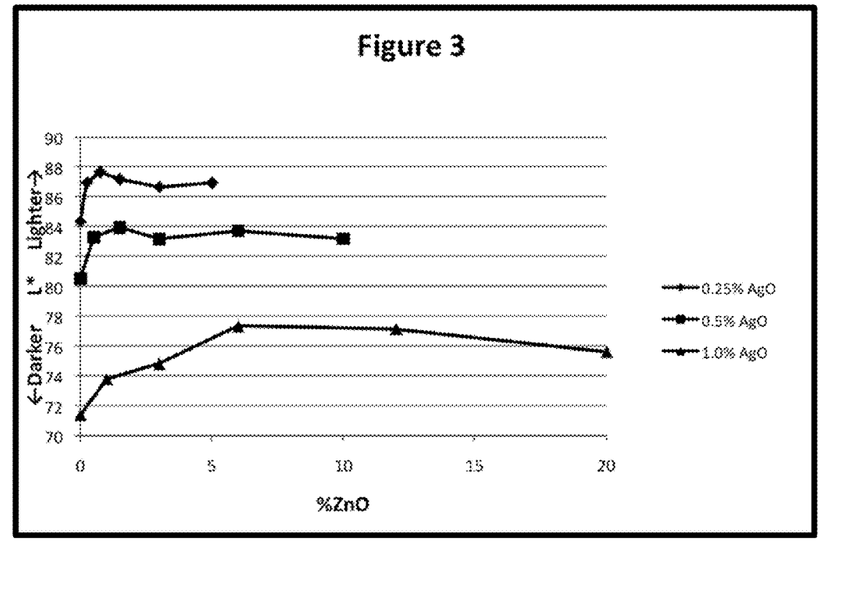
FIG. 3 is a graph plotting whiteness of laundered cloth swatches as a function of the weight content of zinc oxide in the staining formulations initially applied to the swatches.

Thus, the general appearance of the curve of the stained and laundered samples does not parallel or closely follow the general appearance of the curve of the stained samples. Moreover, at high zinc oxide contents or zinc oxide to silver(II) oxide ratios, the formulation whiteness appears to decrease with increasing zinc oxide content or ratio, instead of continuing to increase, as in the stained samples. Without wishing to be limited by theory, I attribute this to the tendency of the zinc oxide particles to adhere to the fabric, compounded by the tendency of the silver(II) oxide particles to adhere to, or otherwise associate with, the zinc oxide particles. Even so, the zinc oxide does not appear to reduce or appreciably reduce the anti-microbial efficacy of the silver(II) oxide.

An exemplary general procedure for producing the inventive silver oxide based cream is as follows: a liquid wax ester such as jojoba oil or hydrogenated jojoba oil is heated, preferably to around 80° C. A wax such as beeswax is preferably melted into the liquid wax ester. The material is mixed thoroughly as it is cooled below about 60° C. An essential oil such as palmarosa oil may be added. Mixing is continued as zinc oxide is introduced along with a silver oxide such as a silver (II) oxide or a silver (I) oxide, and the mixing may be continued during cooling of the mixture to below about 40° C. The mixing may advantageously produce an intimately dispersed formulation in which the silver oxide and/or the zinc oxide may be distributed in a homogeneous or substantially homogeneous fashion within the carrier medium.

Typically, the formulations contain 0.05% to 3% silver oxide, by weight, and more typically, 0.1% to 3% silver oxide. The formulations also contain 1% to 22% zinc oxide, by weight, and more typically, 1% to 20% zinc oxide.

EXAMPLES

Reference is now made to the following examples, which together with the above description, illustrate the invention in a non-limiting fashion.

Example 1

The exemplary silver oxide-zinc oxide formulations provided hereinbelow were prepared according to the following general procedure: jojoba oil is heated to 80° C. A wax such as beeswax may then be introduced. The material is mixed thoroughly as it is cooled to about 55° C. Palmarosa oil is added, followed by silver (II) oxide and zinc oxide. Mixing may be maintained throughout, and during cooling of the mixture to 35° C.-40° C.

In these exemplary formulations, the weight ratio of the liquid wax ester to beeswax is about 3.5 to 1. The palmarosa oil content is about 0.07% of the jojoba oil content.

Examples 2-13

Using the general procedure provided in Example 1, various silver oxide-zinc oxide formulations were prepared. Some of the specific formulations are provided below, by way of example, in Table 5. Formulations that have not been provided below produced qualitatively similar results. The percentages of silver oxide and zinc oxide are by weight, based on the total weight of the final product.

Visual whiteness evaluations were performed on each of the samples, using the scale provided in Table 6.

Example 14

The exemplary silver oxide-zinc oxide formulations provided hereinbelow were prepared according to the following general procedure: to a container containing water is added a viscosity-building agent, typically a smectite (e.g., a bentonite or montmorillonite powder such as Gelwhite H, produced by Southern Clay Products, Inc., Gonzales, Tex.). Other viscosity-building clays, particularly clays in which the silicate layers are disposed in a sandwiched structure, may also be used. Other viscosity-building agents and thickeners may be used, e.g., glycerin and carbomers. Preferably, such selected materials may exhibit good resistance to oxidation or chemical attack by the highly reactive silver(II) oxide.

The mixture is mixed or homogenized, typically for 0.5 to 2 hours. Silver(II) oxide may be introduced at this stage of the processing. Zinc oxide may be introduced to the mixture, typically along with the silver(II) oxide, or sometime therebefore or thereafter. The oil and/or liquid wax ester (e.g., jojoba oil) may be introduced to the mixture during the mixing (e.g., blending or homogenizing).

TABLE 5

| | Silver Oxide | Zinc Oxide | Wt. Ratio | Whiteness | Spreadability |
|---|---|---|---|---|---|
| Example 2 | 1.00% | 3.00% | 1 to 3 | 4 | Excellent |
| Example 3 | 0.50% | 3.00% | 1 to 6 | 6 | Excellent |
| Example 4 | 0.25% | 3.00% | 1 to 12 | 8 | Excellent |
| Example 5 | 1.00% | 7.00% | 1 to 7 | 6 | Excellent |
| Example 6 | 0.50% | 7.00% | 1 to 14 | 7 | Excellent |
| Example 7 | 0.25% | 7.00% | 1 to 28 | 8 | Excellent |
| Example 8 | 1.00% | 12.00% | 1 to 12 | 8 | Good |
| Example 9 | 0.50% | 12.00% | 1 to 24 | 9 | Good |
| Example 10 | 0.25% | 12.00% | 1 to 48 | 10 | Good |
| Example 11 | 1.00% | 20.00% | 1 to 20 | 8 | Less Good |
| Example 12 | 0.50% | 20.00% | 1 to 40 | 10 | Less Good |
| Example 13 | 0.25% | 20.00% | 1 to 80 | 10 | Less Good |

TABLE 6

| 1 | 2 | 3 | 4 | 5 | 6 | 7 | 8 | 9 | 10 |
|---|---|---|---|---|---|---|---|---|---|
| Charcoal/ black gray | Very dark gray | Dark gray | Slightly dark gray | Gray | Light gray | Slightly gray | Off white | White | Very white |

Mixing may be continued as the silver(II) oxide is introduced, and further mixing may ensue, typically for 5-30 minutes. The mixing may advantageously produce an intimately dispersed formulation in which the silver oxide and/or the zinc oxide may be distributed in a homogeneous or substantially homogeneous fashion within the carrier medium. The formulation may then be poured into storage containers.

Example 15

Using the general procedure provided in Example 14, a water-based silver(II) oxide-zinc oxide formulation was prepared. The formulation included:

| | |
|---|---|
| water: | 600 grams (87.1%) |
| bentonite: | 25 grams (3.6%) |
| jojoba oil: | 15 grams (2.2%) |
| zinc oxide: | 40 grams (5.8%) |
| silver(II) oxide: | 9 grams (1.3%) |

Example 16

Using the general procedure provided in Example 14, an emulsion-based silver(II) oxide-zinc oxide formulation was prepared. The formulation included:

| | |
|---|---|
| water: | 600 grams (63.1%) |
| bentonite: | 60 grams (6.3%) |
| jojoba oil: | 240 grams (25.2%) |
| zinc oxide: | 50 grams (5.3%) |
| silver(II) oxide: | 0.9 grams (0.1%) |

Example 17

A control group of thirty patients was treated at Irvine3 Circulation/Vascular Labs (Chieti-Pescara University, Pescara, Italy) using conventional cleaning and compression management methods.

The ulcerations of the patients were diagnosed as resulting from reduced arterial pressure (above-necrosis limits with average skin perfusion pressure >50 mmHg) and diabetic microangiopathy, and were characterized by localized infection.

Color duplex scanning was used to exclude venous thrombosis, severe arterial obstruction, and Doppler techniques were used to evaluate the presence of tibial pulses, to exclude patients with severe ischemia and necrosis.

The study of the microcirculation was used to quantify microangiopathy and to follow up subjects after local treatment. Laser Doppler Flowmetry (LDF) was used to assess skin perfusion in association with transcutaneous oxygen (PO2) measurements.

Example 18

The efficacy of an ointment containing silver tetroxide (AgO) applied onto the skin surrounding the ulceration was tested at the Irvine3 Circulation/Vascular Labs on a treatment group of 29 patients, having comparable ulcerations to those of the control group of Example 17.

The ointment, containing approximately 1% AgO was applied around and at the edge of the ulcerated areas (maximum diameter ranging between 2 cm and 1.1 cm) and on the ulceration, after cleaning, three times daily. The cream was applied after careful washing for 2 minutes in water at 40° C. with a sodium hypochlorite based disinfectant (Amuchina®, Angelini Group, Italy) of the ulceration and surrounding area. A neutral adsorbing paper bandage—in contact with the skin—was applied under a skin protecting/saving foam layer. An adhesive bandage or an elastic stocking was used to cover the ulcerated area during the observation period.

Over the course of the 4-week treatment period, treatment with the AgO ointment was found to be more effective than the wound care used in the controls. The skin PO2 was increased (28%), and LDF (abnormally increased around the ulcerated areas) was decreased (median 29%). Flux increase is generally associated with severe microangiopathy. The venoarteriolar response of the area was significantly reduced (<30%) at inclusion and improved at the end of the four weeks in the treatment group (+16%).

The ulcer areas were significantly smaller at 4 weeks (the maximum diameter range was between 0.23 cm and 0; $p<0.05$) in the AgO-treated group with complete closure in 39% of subjects, vs. 16% in the controls ($p<0.05$).

Example 19

The efficacy of a silver tetroxide-zinc oxide (AgO—ZnO) ointment on skin ulcers was tested at the Irvine3 Circulation/Vascular Labs on a treatment group of 18 patients, versus a control group having 23 comparable patients. All patients underwent basic wound care treatment including conventional cleaning and compression management methods.

The ointment, containing 0.99% AgO and 5.0% ZnO in a beeswax and jojoba oil base, was applied around and at the edge of the ulcerated areas (maximum diameter ranging between 2-3 cm and 0.4 cm) and on the ulceration, after cleaning, twice daily. A neutral adsorbing paper bandage—in contact with the skin—was applied under a skin protecting/saving foam layer. An adhesive bandage or an elastic stocking was used to cover the ulcerated area during the observation period.

Over the course of the 3-week treatment period, treatment with the AgO—ZnO ointment was found to be more effective than the wound care used in the controls. Moreover, the AgO—ZnO ointment was found to be more effective than a similar ointment containing a comparable concentration of AgO, but no ZnO. The AgO—ZnO ointment was found to improve the microcirculation and healing rate in both venous ulcerations and diabetic ulcerations.

Example 20

The efficacy of a silver tetroxide-zinc oxide (AgO—ZnO) ointment on venous skin ulcers was tested at the Irvine3 Circulation/Vascular Labs on a treatment group of 44 patients, versus a control group having 38 comparable patients. All patients underwent basic wound care treatment including conventional cleaning and compression management methods.

The ointment, containing 0.87% AgO and 6.8% ZnO in a beeswax and jojoba oil base, was applied, twice daily, around and at the edge of the ulcerated areas, after cleaning.

After 4 weeks, the silver tetroxide-zinc oxide treatment proved more effective than the control group treatment: skin PO2 was increased 2.1 times more than the control group (17.4% to 8.2%) and skin flux (RF) was improved 1.6 times with respect to the control group (−38.7% to −24.2%). The total surface area of the ulcer was reduced in the silver treatment group by 88.7%, as opposed to 46.9% in the control group. In addition, in the treatment group, complete closure of the ulceration was observed in 42% of subjects compared to 22% in the control group.

Example 21

The efficacy of the AgO—ZnO ointment of Example 20 on diabetic ulcerations was tested at the Irvine3 Circulation/Vascular Labs on a treatment group of 34 patients, versus a control group having 32 comparable patients. All patients underwent basic wound care treatment including conventional cleaning and compression management methods.

The ointment was applied, twice daily, around and at the edge of the ulcerated areas, after cleaning.

After 4 weeks, the silver tetroxide-zinc oxide treatment proved more effective than the control group treatment: skin PO2 was increased 2.6 times more than the control group (23.3% to 9.1%) and skin flux (RF) was improved 4.3 times with respect to the control group (−26.7% to −6.2%). The total surface area of the diabetic ulcerations was reduced in the silver treatment group by 89.0%, as opposed to 23.9% in the control group. In addition, in the treatment group, complete closure of the ulceration was observed in 39% of subjects compared to 16% in the control group.

Example 22

The anti-microbial efficacy of various formulations was tested and compared using the following colony counting method:

A freshly opened Muller-Hinton nutrient broth (liquid medium) was inoculated using a loop full of bacteria (around 100,000-150,000 count). The sample is allowed to rest for 24 hours in the incubator at 37° C. Once the broth is turbid, another full loop is added to several tubes of nutrient broth, and the broth is allowed to sit for 10 minutes.

A known quantity of each tested formulation is applied onto respective sterile blank antibiotic discs. After adding one disc to each one of the tubes, the tubes are swirled and allowed to incubate for 24 hours in an incubator at 37° C.

Once the turbidity (bacterial growth) has been achieved after 24 hours, a loop full of each culture is streaked onto a Muller-Hinton agar plate using the streak plate ("zigzag") method. The use of a standard loop ensures that the same amount of culture is delivered to each plate. The plates are allowed to mature in an incubator for 24 hours at 37° C.

After 24 hours, the colonies are counted by means of two techniques:
- a manual technique in which a number of 100 is assigned to the control sample, and based on the density of the colonies in the other samples, a relative number is assigned based upon visual evaluation.
- an automatic colony counter (WU-14025-00 Flash & Grow Colony Counter, Cole-Palmer®, Vernon Hills, Ill.), which counts the colonies and is accurate up to 99%.

Examples 23-27

The anti-microbial efficacy of various formulations was tested and compared using the procedure detailed in Example 22, using *Enterococcus faecalis* (ATCC 29212) and water-based formulations containing water, bentonite and jojoba oil. The results are provided below, in Table 7:

TABLE 7

| SAMPLE/ EXAMPLE NO. | SAMPLE TYPE | COMPOSITION % AgO | COMPOSITION % ZnO | NUMBER OF COLONIES COLONY COUNTER | NUMBER OF COLONIES VISUAL METHOD |
|---|---|---|---|---|---|
| Nutrient Broth | blank | — | — | 0 | 0 |
| E. Faecalis | control | — | — | 10254 | 100 |
| 23 | silver oxide-zinc oxide | 1.3 | 5.8 | 0 | 0 |
| 24 | silver oxide | 1.4 | — | 0 | 0 |
| 25 | zinc oxide | — | 5.9 | 122 | 2 |
| 26 | silver oxide-zinc oxide | 1.2 | 11.0 | 0 | 0 |
| 27 | silver oxide-zinc oxide | 1.1 | 19.8 | 0 | 0 |

Examples 28-32

The anti-microbial efficacy of various formulations was tested and compared using the procedure detailed in Example 22, using Enterococcus faecalis (ATCC 29212) and oil-based formulations containing beeswax and jojoba oil. The results are provided below, in Table 8:

TABLE 8

| SAMPLE/ EXAMPLE NO. | SAMPLE TYPE | COMPOSITION % AgO | COMPOSITION % ZnO | NUMBER OF COLONIES COLONY COUNTER | NUMBER OF COLONIES VISUAL METHOD |
|---|---|---|---|---|---|
| Nutrient Broth | blank | — | — | 0 | 0 |
| E. Faecalis | control | — | — | 10254 | 100 |
| 28 | silver oxide-zinc oxide | 1.0 | 7.0 | 2755 | 20 |
| 29 | silver oxide | 1.0 | — | 7327 | 70 |
| 30 | zinc oxide | — | 7.0 | 14559 | 120 |
| 31 | silver oxide-zinc oxide | 1.0 | 14.0 | N/A* | 180 |
| 32 | silver oxide-zinc oxide | 0.84 | 28.0 | N/A* | 250 |

*too thick for quantitative measurement by colony counter

It is evident from the counting of the colonies, that zinc oxide without silver(II) oxide (Sample 30) is not particularly effective in reducing the number of colonies, and in fact, a large increase in the number of colonies is observed. It is further evident that while silver(II) oxide alone displays some efficacy in reducing the number of colonies (Sample 29), that efficacy is greatly enhanced in Sample 28, a formulation containing zinc oxide and silver(II) oxide in a 7:1 weight ratio. In the formulations (Samples 31 and 32) containing higher ratios of zinc oxide to silver(II) oxide (about 14:1 to about 33:1), the number of colonies increased greatly, to the point that the number could not be measured by the colony counter.

Example 33

The anti-microbial efficacy of various formulations was tested and compared using a modified pour plate method. The bacterial population of a suspension of each test organism was prepared and determined as follows:

Inoculate the surface of a suitable volume of solid agar medium from a recently revived stock culture of each of the specified microorganisms.

Invert and incubate at 37° C. for 24-48 hours.

Harvest the bacterial cultures, use sterile saline TS or Phosphate Buffer Solution (PBS), wash the surface growth, effect collection in a suitable vessel (e.g., a test tube), and add sufficient sterile saline TS or PBS to obtain a microbial count of about $1\times10^8$ colony-forming units per mL (cfu/ml), which is approximately a McFarland Standard No. 1.0 or visible light transmittance of 47-50% at a wavelength of 580 nm.

Measure the suspension concentration by means of a spectrophotometer and adjust the concentration as needed.

Verify the bacterial population of the inoculum:

Add 9 ml of sterile PBS to each of 8 sterile test tubes using sterile pipettes and bulbs. The tubes are kept closed when not in use to prevent contamination.

Withdraw 1 ml (1000 microliters) from the original culture and add to a first ($10^{-1}$) tube, mixing so that the bacteria are completely suspended therein. Withdraw 1 ml from the first tube and add to a second ($10^{-2}$) tube, mixing as above. Withdraw 1 ml from the second tube and add to a third ($10^{-3}$) tube, mixing as above. Withdraw 1 ml from the third tube and add to a fourth ($10^{-4}$) tube, mixing as above. Withdraw 1 ml from the fourth tube and add to a fifth ($10^{-5}$) tube, mixing as above. Withdraw 1 ml from the fifth tube and add to a sixth ($10^{-6}$) tube, mixing as above. Withdraw 1 ml from the sixth tube and add to a seventh ($10^{-7}$) tube, mixing as above. Withdraw 1 ml from the seventh tube and add to an eighth ($10^{-8}$) tube, mixing as above.

Prepare plates from the serial dilutions as follows:

Dispense 1 ml from the fourth tube onto the surface of the agar and spread the sample over the entire surface using a sterile cell spreader (L-shaped glass rod). To sterilize the cell spreader, dip in ethanol in plate and flame only to burn off the alcohol. Repeat this procedure for two additional plates, by dispensing 1 ml from each of the sixth tube and the eighth tube into respective plates. Allow plates to dry for 5 minutes before inverting for incubation for 24-48 hours at 37° C.

Record the colony counts and calculations as follows:

Identify two plates of the same dilution, having between 30 and 300 colonies. Count the number of bacterial colonies (regardless of size) on that plate, record the results, and calculate the average count. Calculate the approximate number of organisms in the original culture using the average counts in the selected dilution plates.

Pour 20 ml Tryptic Soy Agar (TSA) into each Petri dish (100×15 mm). In a suitable flask or bottle, weigh the desired amount of the dehydrated agar and achieve the concentration recommended by the manufacturer using deionized water.

Place on top of a hot plate having a stirrer and bring the bottle to a boil. After boiling, transfer the bottle to a water bath previously set at 45° C. Monitor the temperature of the agar until the temperature stabilizes at 45° C.

Aseptically weigh out 10 g of the test product in a sterile sample cup. When formulations containing significantly different concentrations of AgO are being compared, the weight of the test product may be adjusted to keep the total amount of AgO constant for all samples. Add inoculum (typically about 0.1 ml) to the test product in the sample cup such that the final concentration of microorganisms in the test product is approximately $1\times10^6$ cfu per gram. Using a sterile glass rod, mix thoroughly to obtain a homogeneous sample.

Aseptically collect 0.1 g of the inoculated test product into the sterile Petri dish at 0, 10, and 30 minutes and at 1, 2, 3, 4, 18 and 24 hours. Add 2 ml of Mueller-Hinton Broth to neutralize the effect of the product, mix well.

Pour 20 ml of TSA (45° C.) into the inoculated Petri dish. Cover and mix thoroughly by gentle tilting and swirling the dish on a flat, level surface. Place at room temperature on a flat surface undisturbed for about 10 minutes to allow the agar to completely gel. Invert and incubate at 37° C. for 24-48 hours.

After 24 hours, the colonies are counted by means of a manual technique in which a number of 100 is assigned to the control sample, and based on the density of the colonies in the other samples, a relative number is assigned based upon visual evaluation.

Examples 34-38

The modified pour plate method of Example 33 was used to evaluate the efficacy of various formulations on test organisms such as Enterococcus faecalis and water-based formulations containing water, bentonite and jojoba oil. The results are provided below, in Table 9:

TABLE 9

| SAMPLE/ | | COMPOSITION | | NO. OF COLONIES |
|---|---|---|---|---|
| EXAMPLE NO. | SAMPLE TYPE | % AgO | % ZnO | VISUAL METHOD |
| E. Faecalis | control | — | — | 100 |
| 34 | silver(II) oxide-zinc oxide | 1.3 | 5.8 | 10 |
| 35 | silver(II) oxide | 1.4 | — | 15 |
| 36 | zinc oxide | — | 5.9 | 80 |
| 37 | silver(II) oxide-zinc oxide | 1.2 | 11.0 | 10 |
| 38 | silver(II) oxide-zinc oxide | 1.1 | 19.8 | 10 |

It is evident from the manual counting of the colonies, that zinc oxide without silver(II) oxide (Sample 36) is not particularly effective in reducing the number of colonies. It is further evident that while silver(II) oxide alone displays efficacy in reducing the number of colonies (Sample 35), that efficacy is greatly enhanced in Sample 34, a formulation containing zinc oxide and silver(II) oxide in or up to a 4.5:1 weight ratio. The formulations containing higher ratios of zinc oxide to silver (II) oxide (about 9:1 to 18:1), also exhibit enhanced efficacy in reducing the number of colonies.

Examples 39-43

The modified pour plate method of Example 33 was used to evaluate the efficacy of various formulations on test organisms such as *Enterococcus faecalis* and oil-based formulations. The results are provided below, in Table 10:

TABLE 10

| SAMPLE/ | | COMPOSITION | | NO. OF COLONIES |
|---|---|---|---|---|
| EXAMPLE NO. | SAMPLE TYPE | % AgO | % ZnO | VISUAL METHOD |
| E. Faecalis | control | — | — | 100 |
| 39 | silver(II) oxide-zinc oxide | 1.0 | 7.0 | 15 |
| 40 | silver(II) oxide | 1.0 | — | 80 |
| 41 | zinc oxide | — | 7.0 | 130 |
| 42 | silver(II) oxide-zinc oxide | 1.0 | 14.0 | 160 |
| 43 | silver(II) oxide-zinc oxide | 0.84 | 28.0 | 180 |

FIG. 5 provides top view photographs of Petri dishes containing oil-based formulations and identically grown cultures according to a modified pour plate method, wherein: FIG. 5A shows a cultured Petri dish after being exposed to a formulation containing 1.0% AgO and 7.0% ZnO (Sample 39); FIG. 5B shows a cultured Petri dish after being exposed to a formulation containing 1.0% AgO and no ZnO (Sample 40); FIG. 5C shows a cultured Petri dish after being exposed to a formulation containing 7.0% ZnO and no AgO (Sample 41); FIG. 5D shows a cultured Petri dish after being exposed to a formulation containing 1.0% AgO and 14.0% ZnO (Sample 42); and FIG. 5E shows a cultured Petri dish after being exposed to a formulation containing 0.84% AgO and 28.0% ZnO (Sample 43).

It is evident from the photographs, and from the manual counting of the colonies, that zinc oxide is not effective in reducing the number of colonies. It is further evident that while silver(II) oxide alone displays efficacy in reducing the number of colonies, that efficacy is greatly enhanced in Sample 39, a formulation containing zinc oxide and silver(II) oxide in or up to a 7:1 weight ratio. However, with formulations containing high ratios of zinc oxide to silver(II) oxide (14:1 or higher, as in Samples 42 and 43), the formulation shows poor efficacy in reducing the number of colonies.

These results have some similarities to the results obtained using water-based formulations, but also exhibit some differences, most notably relating to the performance of formulations having high ratios of zinc oxide to silver(II) oxide. Without wishing to be bound by theory, I believe that in water-based formulations, the available silver(II) oxide concentrations are appreciably higher, such that the high concentration of zinc oxide may not impede, or largely may not impede, the anti-microbial action of the silver(II) oxide. In oil-based formulations, by sharp contrast, the zinc oxide, at high concentrations, may cover or impede the contact of the silver(II) oxide with the microorganisms, and thus compromises the anti-microbial efficacy. At low concentrations of zinc oxide, however, the zinc oxide may act as a solid dispersant with respect to the silver(II) oxide, thereby greatly increasing the available specific surface area thereof, but without substantial covering of the silver(II) oxide particles.

Example 44

The anti-microbial efficacy of various formulations was tested and compared using a Kirby-Bauer type test, as follows:

Ready-made Muller-Hilton agar was streaked with the bacterial inoculum using a sterile applicator. The sample was allowed to sit for 5 minutes to ensure that the bacteria adhere to the surface of the agar. Subsequently, an antibiotic sterile blank disc was pressed against a known quantity of the formulation being tested. While the amount applied to each disc was not measured, care was taken to obtain a consistent amount of material on each disc. Multiple duplicate discs were used to verify the data. The disc was pressed against the surface of the agar, making sure not to damage the disc or the agar. Each agar plate was then inverted and allowed to sit in the incubator at 37° C. for 24 hours. The plates were subsequently removed from the incubator, and the zone of inhibition was measured using a ruler.

Examples 45-46

The anti-microbial efficacy of various oil-based and water-based formulations was tested and compared using the procedure detailed in Example 44, using various individual strains of bacteria such as Enterococcus faecalis and Staphylococcus aureus (ATCC No. 25923).

Two oil-based formulations were tested several times against Enterococcus faecalis: Sample 45, a two-month old sample containing 1.0% AgO and no zinc oxide, disposed in a beeswax and jojoba oil base, and Sample 46, a two-month old sample containing 0.87% AgO and 6.8% ZnO, also disposed in a beeswax and jojoba oil base.

In the case of Sample 45, the zone of inhibition averaged approximately 4 mm; in the case of Sample 46, the zone of inhibition averaged approximately 18 mm. The relatively wide zone of inhibition achieved by Sample 46 indicates improved anti-microbial efficacy with respect to Sample 45, despite a lower total content of AgO.

It would appear that the improved anti-microbial efficacy in these oil-based formulations is attributable to the presence of zinc oxide in Sample 41, and more particularly, to the presence of zinc oxide in a weight ratio of less than 14:1, less than 12:1, and less than 10:1. Without wishing to be bound by theory, I believe that, as stated hereinabove, the zinc oxide may act as a solid dispersant with respect to the silver(II) oxide, thereby greatly increasing the available specific surface area thereof, but—within or below these weight ratios—without substantial covering of the silver(II) oxide particles.

As used herein in the specification and in the claims section that follows, the term "silver (II) oxide" refers to a silver oxide whose unit structure contains silver and oxygen in a substantially 1:1 molar ratio. The term "silver (II) oxide" is specifically meant to include $Ag_4O_4$ (often represented as $Ag_2O_3.Ag_2O$) and AgO.

As used herein in the specification and in the claims section that follows, the term "whiteness value" and the like refers to a whiteness or luminance parameter L*, as specified by the International Commission on Illumination (Commission Internationale d'Eclairage, or CIE), and expressed as a percentage, wherein L*=0 represents black, and L*=100 represents diffuse white.

As used herein in the specification and in the claims section that follows, the term "laundered white cloth" and the like refers to a white cloth swatch that has been stained and laundered substantially according to the staining and laundering procedure described hereinabove.

As used herein in the specification and in the claims section that follows, the terms "homogeneous" and "substantially homogeneous", with respect to a silver oxide formulation, are meant to be used according to their meaning in the art of topical formulation manufacturing.

As used herein in the specification and in the claims section that follows, the term "percent", or "%", refers to percent by weight, unless specifically indicated otherwise.

Similarly, the term "ratio", as used herein in the specification and in the claims section that follows, refers to a weight ratio, unless specifically indicated otherwise.

As used herein in the specification and in the claims section that follows, the term "largely includes", with respect to a component within a formulation, refers to a weight content of at least at least 30%, at least 40%, at least 50%, or at least 60%.

As used herein in the specification and in the claims section that follows, the term "predominantly includes", with respect to a component within a formulation, refers to a weight content of at least at least 50%, at least 65%, at least 75%, or at least 85%.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A topical formulation for application to exposed body tissue, the formulation comprising a silver(II) oxide and zinc oxide, said silver(II) oxide and said zinc oxide intimately dispersed within a carrier medium,
wherein a ratio of said zinc oxide to said silver(II) oxide is at least 0.5:1, by weight.

2. The topical formulation of claim 1, wherein the formulation contains at least 0.05%, by weight, of said silver(II) oxide, and at least 0.05%, by weight, of said zinc oxide.

3. The topical formulation of claim 2, the formulation containing less than 25%, by weight, of said zinc oxide.

4. The topical formulation of claim 1, wherein said ratio of said zinc oxide to said silver oxide(II) is less than 20:1, by weight.

5. The topical formulation of claim 1, the formulation containing less than 3%, by weight, of said silver(II) oxide.

6. The topical formulation of claim 1, wherein said carrier medium includes an oleaginous material.

7. The topical formulation of claim 6, wherein said oleaginous material includes a wax.

8. The topical formulation of claim 1, said carrier medium further including a liquid wax ester.

9. The topical formulation of claim 1, wherein said silver (II) oxide and said zinc oxide are selected, and said silver(II) oxide and said zinc oxide are dispersed within said carrier medium, whereby:

$$L^* \geq (L_0^*) + 2,$$

wherein $L_0^*$ is a baseline whiteness value of the formulation, without said zinc oxide, and $L^*$ is a whiteness value of the formulation, including said zinc oxide.

10. The topical formulation of claim 9, wherein said silver (II) oxide, said zinc oxide, and said carrier medium are selected, and said silver(II) oxide and said zinc oxide are dispersed within said carrier medium, whereby said whiteness value $L^*$ is at least 78.

11. The topical formulation of claim 1, wherein a content of said silver(II) oxide is at least about 0.5%, by weight of the total formulation, and wherein said silver(II) oxide, said zinc oxide, and said carrier medium are selected, and said silver oxide(II) and said zinc oxide are dispersed within said carrier medium, whereby a whiteness value $L^*$ of the formulation is at least 80.

12. The topical formulation of claim 1, wherein a content of said silver(II) oxide is at least about 1.0%, by weight of the total formulation, and wherein said silver(II) oxide, said zinc oxide, and said carrier medium are selected, and said silver (II) oxide and said zinc oxide are dispersed within said carrier medium, whereby a whiteness value $L^*$ of the formulation is at least 75.

13. The topical formulation of claim 1, wherein said silver (II) oxide, said zinc oxide, and said carrier medium are selected, and said silver(II) oxide and said zinc oxide are dispersed within said carrier medium, whereby a whiteness value $L^*$ of the formulation is at least 82.

14. The topical formulation of claim 1, wherein said carrier medium includes an aqueous phase.

15. The topical formulation of claim 1, said carrier medium further including a hydrogenated liquid wax ester.

16. The formulation of claim 4, wherein said ratio of said zinc oxide to said silver(II) oxide is at least about 1:1, by weight.

17. The formulation of claim 2, wherein the formulation contains less than about 12% of said zinc oxide, by weight of the total formulation.

18. The topical formulation of claim 1, wherein said ratio of said zinc oxide to said silver(II) oxide is less than about 12:1, by weight.

19. A method of treating skin tissue, comprising the steps of:
(a) providing the formulation of claim 1, and
(b) applying the formulation to the skin tissue to effect a treatment of the skin tissue.

20. A topical formulation for application to exposed body tissue, the formulation comprising at least 0.05% silver(II) oxide, by weight, and zinc oxide, said silver(II) oxide and said zinc oxide intimately dispersed within a carrier medium,
wherein a ratio of said zinc oxide to said silver(II) oxide is at least about 1:1, by weight, and less than about 20:1, by weight.

* * * * *